United States Patent [19]

Lerou

[11] Patent Number: 5,036,036

[45] Date of Patent: Jul. 30, 1991

[54] CHROMIUM OXIDE CATALYST COMPOSITION

[75] Inventor: Jan J. Lerou, Chadds Ford, Pa.

[73] Assignee: E. I. Du Pont de Nemours and Company, Wilmington, Del.

[21] Appl. No.: 365,594

[22] Filed: Jun. 13, 1989

[51] Int. Cl.$^5$ .......................... B01J 23/02; B01J 23/26
[52] U.S. Cl. ..................................... 502/317; 502/319
[58] Field of Search ................. 502/317, 319; 423/607

[56] References Cited

U.S. PATENT DOCUMENTS

| | | | |
|---|---|---|---|
| 2,418,309 | 4/1947 | Matuszak et al. | 502/319 X |
| 3,190,840 | 6/1965 | Biais et al. | 502/317 X |
| 3,258,500 | 6/1966 | Swamer et al. | 260/653.7 |
| 3,755,477 | 8/1973 | Firth et al. | 260/653.4 |

FOREIGN PATENT DOCUMENTS 1307224  2/1973  United Kingdom ................ 502/319

*Primary Examiner*—W. J. Shine
*Attorney, Agent, or Firm*—James E. Shipley

[57] ABSTRACT

An improved $Cr_2O_3$ catalyst composition, prepared by pyrolysis of ammonium dichromate, which contains less than 100 ppm of alkali metal and is useful in HF hydrofluorination reactions.

5 Claims, No Drawings

CHROMIUM OXIDE CATALYST COMPOSITION

FIELD OF THE INVENTION

An improved $Cr_2O_3$ catalyst composition, prepared by pyrolysis of ammonium dichromate, which contains less than 100 ppm of alkali metal and is useful in HF hydrofluorination reactions.

BACKGROUND OF THE INVENTION

U.S. Pat. No. 3,755,477 describes a process for producing fluorinated aliphatic hydrocarbons which comprises fluorinating a halogenated aliphatic hydrocarbon, including tetrachloroethylene and chlorotrifluoroethylene, by reaction in the gas phase with HF in the presence of a steam-treated and calcined chromium oxide catalyst prepared by a multi-step process. Example 23, column 5, shows tetrachloroethylene as a raw material with formation of $CF_3CHCl_2$ (20%), $CF_3CHClF$ (20%), $CF_3CHF_2$ (30%), and $CF_3CClF_2$ (20%) at 10/1 $HF/C_2Cl_4$ mol ratio, 5.4 seconds contact time and 360° C. reaction temperature. Example 24, column 5, shows chlorotrifluoroethylene as a raw material with formation of $CF_2=CF_2$ (20%) and $CF_3CHClF$ (13%) at 1.8/1 $HF/C_2ClF_3$ ratio, 4 seconds contact time and 320° C. reaction temperature. In these examples, less desirable pentafluorinated products are obtained in a greater amount than the desired tri-and tetrafluoro products.

U.S. Pat. No. 3,258,500 describes a process for the catalytic vapor phase reaction of HF with halohydrocarbons, including tetrachloroethylene and chlorotrifluoroethylene, employing a catalyst that consists essentially of a heat-activated anhydrous chromium (III) oxide which may be supported on alumina. This catalyst is highly active. Example 17, column 14 showing fluorination of tetrachloroethylene with this catalyst, like that of the above '477 patent, produces large quantities of the less desirable highly fluorinated pentafluoroethane. At 400° C. the product distribution is 35.0% pentafluoroethane, 9.2% 1-chloro-1,2,2,2-tetrafluoroethane, and 3.5% 1,1-dichloro-2,2,2-trifluoroethane. At 300° C. the product distribution is 38.3% 1-chloro-1,2,2,2-tetrafluoroethane, 25.4% pentafluoroethane, and 16.0% 1,1-dichloro-2,2,2-trifluoroethane. Example 20, column 15, shows that chlorotrifluoroethylene yields $CF_3CHF_2$ as the major product at 400° C.

U.S. Pat. No. 3,591,646 discloses the use of catalysts, such as oxides of chromium, for preparation of chlorofluoroethanes by the catalytic reaction, in the gaseous phase, of acetylene, HF and chlorine in the presence of a recycle mixture of halogenated hydrocarbons. In column 2, lines 24–26, it is stated that the catalyst can be associated with modifiers which enhance its activity. Some examples of modifiers are fluorides of potassium, sodium, lithium and cesium. Claim 6 discloses a calcinated and fluorinated alumina catalyst which is impregnated with ammonium dichromate.

These catalyst are not entirely satisfactory in terms of fluorinating activity and catalyst life.

SUMMARY OF THE INVENTION

What has been discovered is a catalyst composition comprising $Cr_2O_3$ prepared by pyrolysis of $(NH_4)_2Cr_2O_7$ and containing an alkali metal content of 100 ppm or less.

More specifically, the instant catalyst composition may be prepared wherein the alkali metal content is obtained by treating $Cr_2O_3$ containing more than 100 ppm of alkali metal content to reduce the alkali metal content to 100 ppm or less.

Also, the present catalyst composition may be obtained by first treating $(NH_4)_2Cr_2O_7$ containing 60–2000 ppm alkali metal to reduce its alkali metal content to less than 60 ppm and thereby results in a $Cr_2O_3$, formed by pyrolysis, containing 100 ppm or less of alkali metal content.

DETAILS OF THE INVENTION

The $Cr_2O_3$ catalyst of this invention is prepared by pyrolysis of ammonium dichromate by any method known to the art including methods such as that described in U.S. Pat. No. 4,741,985, incorporated herein by reference.

By pyrolysis is meant heating ammonium dichromate to a sufficient temperature and for a sufficient time to cause the following reaction to occur to substantial completion:

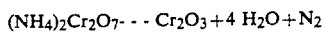

$$(NH_4)_2Cr_2O_7 \rightarrow Cr_2O_3 + 4 H_2O + N_2$$

For example, ammonium dichromate may be heated in a continuous kiln at 500°–700° C., preferably 540°–640° C., for 5–20 minutes so that it will undergo an internal oxidation-reduction reaction to produce mainly water, nitrogen and $Cr_2O_3$. After the water and nitrogen are driven off, the remaining fine powder of $Cr_2O_3$ may be cooled and compacted so as to increase its bulk density for ease of handling. For example, a bulk density of approximately 400–560 $kg/m^3$ may be desirable, preferably 448–512 $kg/m^3$.

The $Cr_2O_3$ obtained may contain low levels of contaminants which are present as a result of the manufacturing process for the original $(NH_4)_2Cr_2O_7$. Although not totally destructive of catalyst efficacy, potassium, for example, as a contaminant has an adverse effect on the activity and life of the catalyst of this invention. It is desirable for the amount of potassium and other alkali metals to be 100 ppm by weight or less. The level may be reduced by a water washing step. While the conditions are not critical, the water washing step can include forming a slurry containing 5–15% $Cr_2O_3$, preferably 10%, and deionized water. Stirring of this water slurry can be carried out at 35°–65° C. for at least one hour, preferably two or more hours. The solids are then recovered by filtration, suitably on a plate and frame filter press. The filter cake can be analyzed for alkali metal content. If its level is 100 ppm by weight or less (dry basis), the solids are, thereafter, dried. If not, the washing step can be repeated to obtain a desired level of alkali metal content.

The form of the catalyst is not critical and may be used as pellets, powders or granules.

For example, if the catalyst is desired to be in the pellet form, 5–15%, preferably 10%, of chromium acetate and 1–5%, preferably 2%, of graphite can be added to the dried solids as pelletization aids. The chromium acetate can be added in aqueous solution of 30–70%, preferably 50% concentration. The resultant paste can be mulled to mix the ingredients and then pelletized to the desired size, preferably 0.32 cm×0.32 cm cylinders. The pellets can be dried at 80°–120° C., preferably 105° C., for 8–48 hours, preferably 16–24 hours. The $Cr_2O_3$ pellets then have a bulk density of 1120–1440 $kg/m^3$ for the preferred pellet size and a surface area of 40–57 m²/g, preferably 45-55 m²/g. Pore volume is 0.15-0.3 cc/g, the alkali metal content is 100 ppm or less.

Generally, the resulting $Cr_2O_3$ catalyst is useful in the HF hydrofluorination of chloromethanes, chloroethanes and chloropropanes. More specifically, the catalyst can be used in processes as diclosed in U.S. Pat. Nos. 3,755,477, 4,129,603, 3,258,500 and British Patent No. 2,030,981 which are incorporated herein by reference.

EXAMPLES

In the following illustrative Examples all parts and percentages are by weight and all temperatures are Centigrade unless otherwise stated. All reactions used commercial HF containing only trace amounts of water.

The pyrolyzed $Cr_2O_3$ catalyst used in the following Examples was prepared using ammonium dichromate having the following specifications:

| | | |
|---|---|---|
| $(NH_4)_2Cr_2O_7$ | | 99.5% |
| Insolubles | less than | 0.2% |
| Iron | less than | 100 ppm |
| Chloride | less than | 100 ppm |
| Sulfate | less than | 100 ppm |
| Alkali metals | | 60 to 2000 ppm |
| pH (8 wt % aqueous sol) | | 3.2-4.0 |

The preparation, purification, drying and compacting of the $Cr_2O_3$ used in the following Examples were performed according to the following procedure:

A rotating continuous kiln, 18 inches in diameter and 17 feet long, was electrically heated to 570°-620° C. At this point the heater was turned off and ammonium dichromate was fed into the kiln at a feed rate of 280 lb/hr (residence time = 8 minutes). The conversion of ammonium dichromate to $Cr_2O_3$ was essentially quantitative. The heat generated from the internal oxidation-reduction reaction to produce water, nitrogen and $Cr_2O_3$ was sufficient to maintain the desired reaction temperature. After the water and nitrogen were driven off, the remaining fine powder of $Cr_2O_3$ was cooled and compacted to a bulk density of approximately 448-512 kg/cubic meter.

The water washing step includes forming a slurry containing 5-15% $Cr_2O_3$ and deionized water. Stirring of this water slurry is conveniently carried out at 35°-65° C. for at least one hour. The solids are then recovered by filtration, suitably on a plate and frame filter press. The filter cake is then analyzed for alkali metal content. If its content is 100 ppm by weight or less (dry basis), the solids are satisfactory for drying and pelletizing. If not, the washing step is repeated to obtain a desired level of alkali metal content.

The catalyst is then dried in an oven at 500° to 650° C. Thereafter, the catalyst is converted into a pellet form by mixing it with 5-15% alkali metal-free chromium acetate and 1-5% of graphite as pelletization aids. The chromium acetate is added as a 30-70% aqueous solution. The resultant paste is mulled to mix the ingredients and then pelletized to a size of 0.32 cm × 0.32 cm cylinders. The pellets are then dried at 80°-120° C. for 8-48 hours, depending upon the temperature. The $Cr_2O_3$ pellets have a bulk density of 1120-1440 kg/m³ and a surface area of 40-57 m²/g. Pore volume is 0.15-0.3 cc/g, the alkali metal content is 100 ppm or less.

PROCEDURE FOR PRETREATMENT

The reactor (0.5 inch ID, 12 inch long "Inconel" pipe) was charged with the amount of catalyst as described in the following Examples and placed in a sand bath. The bath was gradually heated to 400° while nitrogen gas at a flow rate of 50 ml/minute was passed through the reactor to remove traces of water. The temperature was lowered to 200°, and HF and nitrogen gas (1:4 molar ratio) were passed through the reactor. The nitrogen flow was decreased with time until neat HF was being passed through the reactor. At this point, the temperature was gradually raised to 450° and maintained there for 15 to 300 minutes.

PROCEDURE FOR FLUORINATION

The temperature was then decreased, while maintaining the HF flow, to the indicated values and, thereafter, $CCl_2=CCl_2$ flow was started. The flows of HF and $CCl_2=CCl_2$ were adjusted to give the indicated molar ratios and contact times.

The reactor effluent was scrubbed with aqueous potassium hydroxide to remove HCl and HF, and sampled on-line with a gas chromatograph using a 20 foot, long one-eighth inch diameter column containing "Krytox" perfluorinated polyether on an inert support and a helium carrier gas flow of 35 cc/minute.

EXAMPLES 1-7

The Procedures for Pretreatment and Fluorination were followed using 38.1 g (30 cc) of $Cr_2O_3$ with a potassium content of 60 ppm as the initial catalyst charge in the form of crushed pellets (40-80 mesh). The results are given in the Table.

TABLE

| | Example | | | | | | |
|---|---|---|---|---|---|---|---|
| | 1 | 2 | 3 | 4 | 5 | 6 | 7 |
| Temperature | 300° | 300° | 250° | 225° | 225° | 225° | 250° |
| $HF/C_2Cl_4$ mol ratio | 4/1 | 4/1 | 4/1 | 6/1 | 10/1 | 6/1 | 6/1 |
| Contact time (sec.) | 15 | 30 | 60 | 60 | 60 | 90 | 90 |
| Conversion (percent) | 79.8 | 89.4 | 97.8 | 94.9 | 90.4 | 98.3 | 99.5 |
| | Area Percent | | | | | | |
| $CF_3CHCl_2$ | 65.3 | 57.9 | 76.1 | 73.1 | 74.2 | 78.3 | 68.3 |
| $CF_3CHClF$ | 11.8 | 13.2 | 14.5 | 10.0 | 10.0 | 12.4 | 20.2 |
| $CF_3CHF_2$ | 10.7 | 15.1 | 5.4 | 0.1 | 0.1 | 0.1 | 8.0 |
| $CF_3CHCl_2$ + $CF_3CHClF$ | 77.1 | 71.1 | 90.6 | 83.1 | 84.2 | 90.7 | 88.5 |

EXAMPLE 8

A 10 g portion of the catalyst of this invention containing less than 10-20 ppm potassium and 10-45 ppm sodium, crushed to 10-20 mesh particle size, was put in a 3/8 inch "Inconel" 600 reactor immersed in a sand bath. The catalyst was dried and pretreated with HF at 450° C. The experiment started at 350° C. The temperature was increased daily by 25° C. until 450° C. was reached. HF flow rate was 48 sccm; 2,2-dichlorohexafluoropropane (reactant) flow rate was 9.5 g/hr. The effluent of the reactor was analyzed by an on-line gas chromatograph for 2-chloroheptafluoropropane (product) content.

The conditions of this experiment were duplicated using essentially the same catalyst as described herein except it contained 33-70 ppm potassium and 140-160 ppm sodium. The results from both experiments are shown in the following Table:

TABLE

| Temp., °C. | Yield of product (%) | |
| --- | --- | --- |
| | Invention Catalyst | Non-invention Catalyst |
| 350 | 0.70 | 0.44 |
| 375 | 2.45 | 1.84 |
| 400 | 6.67 | 5.09 |
| 425 | 18.0 | 14.3 |
| 450 | 36.6 | 31.5 |

EXAMPLE 9

Fluorination of 1,1,2-trichlorotrifluoroethane at 420° C. with HF over the pretreated catalyst of this invention gives 55–60 percent conversion to pentafluorochloro- and hexafluoroethanes, whereas catalysts with greater than 100 ppm alkali metal gives 50 percent conversion or less under the same process conditions.

These Examples show the superior performance of the invention catalyst.

I claim:

1. A catalyst composition comprising $Cr_2O_3$ prepared by pyrolysis of $(NH_4)_2Cr_2O_7$ and containing an alkali metal content of 100 ppm or less.

2. The catalyst composition of claim 1 wherein the alkali metal content is obtained by treating $Cr_2O_3$ containing more than 100 ppm of alkali metal content to reduce the alkali metal content to 100 ppm or less.

3. The catalyst composition of claim 1 wherein the catalyst composition is obtained by first treating $(NH_4)_2Cr_2O_7$ containing 60–2000 ppm alkali metal to reduce its alkali metal content to less than 60 ppm and thereby results in the $Cr_2O_3$ containing 100 ppm or less of alkali metal content.

4. The catalyst composition of claim 1 where the alkali metal is potassium and sodium.

5. The catalyst composition of claim 2 wherein the treating step is water-washing.

* * * * *